United States Patent
Lee et al.

(10) Patent No.: US 8,172,987 B2
(45) Date of Patent: *May 8, 2012

(54) LOW-ENERGY EXTRACTIVE DISTILLATION PROCESS FOR DEHYDRATION OF AQUEOUS ETHANOL

(75) Inventors: Fu-Ming Lee, Katy, TX (US); Tzong-Bin Lin, Chiayi (TW); Jyh-Haur Hwang, Dali (TW); Hung-Chung Shen, Chiayi (TW); Kuang-Yeu Wu, Plano, TX (US); Lindsey Vuong, Allen, TX (US); Fong-Cheng Su, Chiayi (TW); Po-Sung Cheng, Kaohsiung (TW); Tai-Ping Chang, Cihtong Township (TW)

(73) Assignees: AMT International Inc., Plano, TX (US); CPC Corporation, Taiwan, Taipai (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/184,540

(22) Filed: Jul. 17, 2011

(65) Prior Publication Data
US 2011/0266134 A1    Nov. 3, 2011

Related U.S. Application Data

(63) Continuation of application No. 11/827,896, filed on Jul. 13, 2007, now Pat. No. 8,002,953.

(51) Int. Cl.
*B01D 3/40* (2006.01)
*B01D 3/42* (2006.01)
*C07C 29/84* (2006.01)
*C07C 29/94* (2006.01)
*C12G 3/12* (2006.01)

(52) U.S. Cl. ........ 203/19; 203/22; 203/58; 203/59; 203/60; 203/62; 203/63; 203/64; 203/69; 203/75; 203/77; 203/78; 203/80; 203/99; 203/DIG. 13; 203/DIG. 19; 426/492; 426/493; 426/494; 568/916

(58) Field of Classification Search ............ 203/19, 203/22, 58, 59, 60, 62, 63, 64, 69, 75, 77, 203/78, 80, 99, DIG. 13, DIG. 19; 426/492–494; 568/916

See application file for complete search history.

(56) References Cited

U.S. PATENT DOCUMENTS
4,342,627 A * 8/1982 Cane et al. .................. 203/19
(Continued)

OTHER PUBLICATIONS
Furter W. F., "Extractive Distillation by Salt Effect", Extractive and Azeotropic Distillation, Adv. in Chemistry Series 115, ACS (1972)).
(Continued)

*Primary Examiner* — Virginia Manoharan
(74) *Attorney, Agent, or Firm* — Cascio & Zervas

(57) ABSTRACT

An energy-efficient extractive distillation process for producing anhydrous ethanol from aqueous/ethanol feeds containing any range of ethanol employs an extractive distillation column (EDC) that operates under no or greatly reduced liquid reflux conditions. The EDC can be incorporated into an integrated process for producing anhydrous ethanol used for gasoline blending from fermentation broth. By using a high-boiling extractive distillation solvent, no solvent, is entrained by the vapor phase to the EDC overhead stream, even under no liquid reflux conditions. The energy requirement and severity of the EDC can be further improved by limiting ethanol recovery in the EDC. In this partial ethanol recovery design, ethanol which remains in the aqueous stream from the EDC is recovered in a post-distillation column or the aqueous stream is recycled to a front-end pre-distillation column where the ethanol is readily recovered since the VLE curve for ethanol/water is extremely favorable for distillation.

24 Claims, 5 Drawing Sheets

U.S. PATENT DOCUMENTS

| | | | |
|---|---|---|---|
| 4,349,416 A | | 9/1982 | Brandt et al. |
| 4,359,533 A | * | 11/1982 | Wilke et al. .................. 435/161 |
| 4,366,032 A | * | 12/1982 | Mikitenko et al. .............. 203/18 |
| 4,400,241 A | * | 8/1983 | Braithwaite et al. ............ 203/18 |
| 4,559,109 A | * | 12/1985 | Lee et al. ........................ 203/19 |
| 4,568,356 A | * | 2/1986 | Chambers ....................... 44/453 |
| 5,124,004 A | * | 6/1992 | Grethlein et al. ............... 203/19 |
| 5,252,201 A | * | 10/1993 | Sampath ....................... 208/355 |
| 5,294,304 A | * | 3/1994 | Kano et al. ...................... 203/19 |
| 7,666,299 B2 | * | 2/2010 | Wu et al. ....................... 208/313 |

OTHER PUBLICATIONS

I.D.Gil et al., "Separation of ethanol and water by extractive distillation with salt and solvent as entrainer: process simulation." Brazilian J. Chem. Eng. vol. 25, No. 01, Mar. 2008, pp. 207-215.

* cited by examiner

LOW-ENERGY EXTRACTIVE DISTILLATION PROCESS FOR DEHYDRATION OF AQUEOUS ETHANOL

REFERENCE TO RELATED APPLICATIONS

This application is a continuation of U.S. patent application Ser. No. 11/827,896 that was filed on Jul. 13, 2007 and which is now U.S. Pat. No. 8,002,953.

FIELD OF THE INVENTION

The present invention relates to an improved, energy efficient extractive distillation process for recovering anhydrous (99.5+ wt %) ethanol, that is suitable for gasoline blending, from an aqueous ethanol feedstock, including fermentation broth.

BACKGROUND OF THE INVENTION

Higher oil prices and more stringent environmental regulations have been the impetus for allocating greater resources into research and development for alternate and renewable fuels worldwide. An important development in this regard is the use of ethanol as the blending stock for gasoline. Burning ethanol instead of gasoline could reduce carbon emissions by more than 80% and completely eliminate the release of acid-rain-causing sulfur dioxide. The U.S. Department of Energy (DOE) predicts that ethanol could reduce gasoline consumption by 30% in the United Sates by 2030. A recent DOE report concluded that, in terms of key energy and environmental benefits, fermentation ethanol is clearly superior to petroleum-based fuels, and future cellulosic-based ethanol will be even better.

A major drawback of using ethanol is that fermentation yields dilute aqueous ethanol mixtures that contain only 10-12 wt % ethanol. Current dehydration strategies, for producing anhydrous (99.5 wt %) ethanol that is suitable for gasoline blending, are energy intensive and employ conventional distillation and a subsequent step to break the ethanol-water azeotrope. As compared to the energy value of ethanol which is 21,400 KJ/L, conventional distillation requires approximately 6,400 KJ/L to concentrate fermentation ethanol to 95.6 wt % ethanol, which is the azeotropic composition. Even improved distillation schemes that employ heat integration still require 5,500 KJ/L to produce the azeotropic composition. Thereafter, concentrating the ethanol from the azeotropic point to produce anhydrous ethanol requires more energy. As is apparent, despite the benefits of using ethanol, the energy costs associated with dehydrating ethanol present serious economic impediments for using ethanol produced by fermentation as a gasoline blending stock or as an engine fuel.

The major commercial methods for concentrating ethanol beyond the azeotropic composition for producing anhydrous ethanol are: (1) azeotropic distillation, (2) molecular sieves adsorption, and (3) extractive distillation. A fourth method known as membrane separation which uses zeolitic or polymer membranes to break the azeotrope is largely in the developmental stages.

In azeotropic distillation, a volatile entrainer is added to an aqueous ethanol feed mixture. The entrainer modifies the activity coefficients of the water and ethanol being separated and forms an azeotrope with the water to be taken overhead as the process yields anhydrous ethanol. Pentane, benzene, diethyl ether, and gasoline have been disclosed as suitable entrainers. See, U.S. Pat. No. 3,575,818 to West, U.S. Pat. No. 2,012,199 to McElroy, U.S. Pat. No. 2,371,010 to Wolfner, and Black et al., "Extractive and Azeotropic Distillation," Am. Chem. Soc. Advances In Chemistry Series No. 115, p. 64, 1972. The major disadvantage of the azeotropic method is that the ethanol feed has to be pre-concentrated to near 95 wt %, the azeotropic composition, which is an energy intensive process in itself.

Adsorptive separation processes for separating of ethanol from water are typically batch processes, with respect to the adsorbents used, that entail an adsorption cycle and a separate desorption cycle. Various adsorptive separation techniques are described in, for example, U.S. Pat. No. 4,273,621 to Formoff, U.S. Pat. No. 4,407,662 to Ginder, U.S. Pat. No. 4,465,875 to Greenbank et al., U.S. Pat. No. 4,287,089 to Convers et al., U.S. Pat. No. 4,277,635 to Oulman, U.S. Pat. No. 4,382,001 to Kulprathipanja et al., U.S. Pat. No. 5,030,775 to Sircar, U.S. Pat. No. 4,343,623 to Kulprathipanja et al, U.S. Pat. No. 4,319,058 to Kulprathipanja et al, U.S. Pat. No. 5,766,895 to Valkanas et al, U.S. Pat. No. 4,359,593 to Feldman and U.S. Pat. No. 2,137,605 to Derr. Although adsorption methods are very selective in removing water or ethanol, the associated high heat energy requirements, high operating costs, limited capacities, and uncertainty in the lengths of adsorbent lives are major drawbacks toward commercial operations.

Finally, in extractive distillation (ED) a high-boiling, polar, nonvolatile solvent is added to the upper portion of an extractive distillation column (EDC), while the feed containing ethanol and water is fed the middle or lower portion of the EDC, which is below the solvent entry point. Depending upon the properties of the solvent, the descending nonvolatile solvent preferentially extracts water or ethanol from the ascending vapor stream thereby eliminating the ethanol-water azeotrope and producing purified ethanol or water from the overhead of EDC. A portion of the EDC overhead stream is recycled to the top of the EDC as reflux. Saturated solvent that is rich in water or ethanol is then withdrawn from the bottom of EDC and transferred to the middle portion of a solvent recovery column (SRC). Water or ethanol in the saturated solvent is stripped from the solvent by heat from a SRC reboiler and then recovered from the overhead stream of the SRC as purified water or ethanol. Again, a portion of the overhead stream is recycled to the top of SRC as liquid reflux. Lean solvent from the bottom of SRC is circulated back to the EDC as the solvent feed.

An ED process for dehydrating aqueous ethanol using glycerin as the ED solvent was disclosed in U.S. Pat. No. 1,469,447 to Schneible. Subsequently, other ED solvents considered include: ethoxyethanol and butoxyethanol (U.S. Pat. No. 2,559,519 to Smith et al.), butyl, amyl or hexyl alcohols (U.S. Pat. No. 2,591,671 to Catterall), gasoline components (U.S. Pat. No. 2,591,672 to Catterall), sulfuric acid, acetone or furfural (U.S. Pat. No. 2,901,404 to Kirshenbaum et al.), 2-phenyl phenol, or mixtures of 2-phenyl phenol and cumyl phenol (U.S. Pat. No. 4,428,798 Zudkevitch et al.), cyclohexylcyclohexanone or cyclohexylcyclohexanol (U.S. Pat. No. 4,455,198 to Zudkevitch et al.), methyl benzoate, mixture of methyl benzoate and trimellitic anhydride, and mixture of dipropylene glycol dibenzoate, ethyl salicylate and resorcinaol (U.S. Pat. No. 4,631,115 to Berg et al.), hexahydrophthalic anhydride, mixture of methyl tetrahydrophthalic anhydride and pentanol-1, and mixture of trimellitic anhydride, ethyl salicylate and resorcinol (U.S. Pat. No. 4,654,123 to Berg et al.); and diaminobutane, 1,3-diaminopentane, diethylenetriamine, and hexachlorobutadiene (U.S. Pat. No. 6,375,807 to Nieuwoudt). The ED solvents disclosed in these patents were said to be particularly selective in separating ethanol and water, but without regard to their practical applicability to ED processes with respect to other important solvent properties such as solvent thermal stability, toxicity, boiling point, etc. These patents also did not address energy and related economics issues related to ED processes.

In order to reduce the energy requirements in ED processes, U.S. Pat. No. 4,400,241 to Braithwaite et al. proposed adding alkali-metal or alkaline-earth metal salts to a polyhydric alcohol solvent to enhance the ED solvent performance. The preferred systems include (1) sodium tetraborate that is added to ethylene glycol and (2) dipotassium phosphate that is added glycerin.

Other approaches to reducing energy requirements featured improved process designs to recovery energy such as that in U.S. Pat. No. 4,349,416 to Brandt et al. where a first side stream is withdrawn from the EDC, passed in heat exchange with the bottoms from the EDC en route to the SRC and returned to the EDC at a point below the point of the side stream. A second side stream from the EDC is also withdrawn, passed in heat exchange with the bottoms of the SRC and returned to the EDC.

U.S. Pat. No. 4,559,109 to Lee et al. disclosed another approach whereby aqueous ethanol containing 10-12 wt % ethanol is first converted to an 85-90 wt % concentrated vapor in a front-end distillation column which is then fed to an EDC. The front-end distillation column represents the water-rich (lower) portion of the fractionator, while the EDC represents the ethanol-rich (upper) portion of the fractionator. Extractive solvent is added only to the EDC (ethanol-rich portion of the fractionator) where the vapor-liquid equilibrium (VLE) curve is very unfavorable for distillation. The solvent is said to eliminate the binary ethanol-water azeotrope and modify the shape of the ethanol-rich portion of the VLE curves favorably for distillation. The ethanol-water saturated solvent is then completely removed via a rich solvent bottoms stream from the EDC and fed to a SRC (solvent stripper). The vaporous overhead stream of the SRC is said to be recycled directly to an upper portion of the front-end distillation column while lean solvent from the bottom of the SRC is fed to the top of the EDC. In a preferred application of the process, the rich solvent bottoms stream from the EDC which is fed to the SRC contains more than 40 wt % of the ethanol that is present in the vaporous feed to the EDC from the front-end distillation column (or simply more than 40 wt % of the ethanol in the feed to the front-end distillation column).

In practice the techniques described in U.S. Pat. No. 4,559,109 are neither energy nor cost effective because the rich solvent stream, which contains 40 wt % of the feed ethanol, must be vaporized in the SRC and then again in the pre-distillation column. Initially the rich solvent is vaporized in the SRC to separate the solvent from the water and the ethanol, but it has been demonstrated that the water and the ethanol cannot be directly recycled to the pre-distillation column in the form of vapor as stated in the patent. The reason is that the SRC is normally operated under reduced pressures in order to lower the bottoms temperature so as to minimize solvent decomposition. When ethylene glycol is employed as the ED solvent, as shown in FIGS. 5 and 6 of the patent, the SRC should be operated at substantially lowered pressures of about 150 mmHg at the top in order to keep the bottoms temperature below 180° C. The pre-distillation column, on the other hand, is operated at higher pressures than that of the EDC to allow the vapor stream to be fed from the overhead of the pre-distillation column to the EDC, which is preferred procedure as described in the patent. Because of these constraints, the overhead vapor stream of the SRC has to be condensed before it can be pumped into the higher pressured pre-distillation column, where the ethanol content in the condensed SRC recycle stream is re-vaporized. Another problem associated with the process depicted in U.S. Pat. No. 4,559,109 is that there is no liquid reflux for the SRC which causes the upper trays in the SCR to run dry.

Other energy saving ED techniques employ a combination of the basic distillation method along with (1) multi-effect distillation, (2) conventional overhead-to-reboiler heat pumped distillation, (3) azeotropic and extractive distillation, or (4) fermentative production of volatile compounds, which is disclosed in U.S. Pat. No. 4,961,826 to Grethlein et al. All of the energy saving methods in the prior art for the ED process or combination process schemes associated ED methods are either too limited in scope for energy savings or too complicated for practical applications.

SUMMARY OF THE INVENTION

The present invention provides a simple, energy efficient extractive distillation (ED) process for producing anhydrous ethanol (99.5+ wt % ethanol) from aqueous ethanol feeds containing any range of ethanol. The improved ED technique is particularly suited for incorporation into an integrated process for producing anhydrous ethanol, which is suitable for gasoline blending, from fermentation broth which typically contains 1 to 12 wt % and more preferably 10 to 12 wt % ethanol.

The invention is based in part on the discovery that the liquid reflux within an extractive distillation column (EDC) has essentially no effect with respect to separating ethanol and water; rather, when liquid reflux is employed, it functions primarily to knock down the entrained solvent which is otherwise carried by the vapor phase into the EDC overhead stream. A corollary to operating the EDC under no liquid reflux or greatly reduced liquid reflux conditions is that the energy input to the EDC is substantially reduced. An aspect of the invention is that by using a high-boiling ED solvent, no solvent is entrained by the vapor phase to the EDC overhead stream, even under no liquid reflux conditions. A feature of the invention is that the energy requirement and severity of the EDC can be further improved by modifying the process to limit ethanol recovery in the EDC. In this partial ethanol recovery design, ethanol which remains in the aqueous stream from the EDC is recovered in a post-distillation column or the aqueous stream is recycled to a front-end pre-distillation column where the ethanol is readily recovered since the water-rich portion of the vapor-liquid equilibrium curve for ethanol/water is extremely favorable for distillation.

In one embodiment, the invention is directed to an improved extractive distillation (ED) process for dehydrating an aqueous feedstock containing ethanol and water that includes the steps of:

(a) introducing an aqueous feedstock comprising ethanol and water into a middle portion of an extractive distillation column (EDC);

(b) introducing a high-boiling water selective solvent into an upper portion of the EDC to contact the aqueous feedstock under extractive distillation conditions to produce a liquid bottoms stream that comprises water and high-boiling water selective solvent and to produce a vaporous overhead stream that comprises greater than 99.5 weight percent ethanol, wherein the EDC is operated with a liquid reflux-to-distillate ratio of less than about 0.5;

(c) withdrawing at least a portion of the vaporous overhead from the EDC as a purified ethanol product;

(d) feeding at least a portion of the liquid bottoms stream of the EDC into a solvent recovery column (SRC) to remove water therefrom and to yield a lean high-boiling water selective solvent stream; and
(e) recycling at least a portion of the lean high-boiling water selective solvent stream into an upper portion of the EDC.

In another embodiment, the invention is directed to an improved extractive distillation (ED) process for dehydrating an aqueous feedstock containing ethanol and water that includes the steps of:
(a) introducing an aqueous feedstock comprising ethanol and water into a middle portion of an extractive distillation column (EDC);
(b) introducing a high-boiling ethanol selective solvent into an upper portion of the EDC to contact the aqueous feedstock under extractive distillation conditions to produce a liquid bottoms stream consisting essentially of ethanol and high-boiling selective solvent and a vaporous overhead stream comprising essentially of water, wherein the EDC is operated with a liquid reflux-to-distillate ratio of less than about 0.5;
(c) feeding at least a portion of the liquid bottoms stream of the EDC into a solvent recovery column (SRC) to remove ethanol therefrom and to yield a bottoms stream that comprises lean high-boiling ethanol selective solvent and an overhead stream whereby at least a portion of the overhead is withdrawn as a purified ethanol product with higher than 99.5 wt % purity; and
(d) recycling at least a portion of the lean high-boiling ethanol selective solvent from the bottoms stream of the SRC into the upper portion of the EDC.

In a further embodiment, the invention is directed to an improved process for dehydrating an aqueous feedstock containing ethanol and water that includes the steps of:
(a) distilling an aqueous feedstock comprising ethanol and water in a pre-distillation column to produce a first vaporous overhead stream, a vaporous side-cut stream, and a first liquid bottoms stream;
(b) partially condensing the first vaporous overhead stream in a first condenser to yield a condensate phase and a vapor phase;
(c) recycling the condensate phase from the first condenser into the pre-distillation column as reflux;
(d) introducing the vaporous side-cut stream into a middle portion of an extractive distillation column (EDC);
(e) introducing a bottoms stream from a solvent recovery column (SRC) which contains a high-boiling water selective solvent into an upper portion of the EDC to contact the vaporous side-cut stream under extractive distillation conditions to produce a second vaporous overhead stream that comprises greater than 99.5 wt % ethanol and a second liquid bottoms stream comprising water, ethanol and high-boiling water selective solvent wherein the EDC is operated with a liquid reflux-to-distillate (RID) ratio of less than about 0.5;
(f) introducing at least a portion of the second liquid bottoms stream from the EDC that comprises water, ethanol and high-boiling water selective solvent into the SRC to remove water and ethanol from the high-boiling water selective solvent;
(g) recycling at least a portion of a bottoms stream of the SRC that comprises high-boiling water selective solvent into an upper portion of the EDC;
(h) recycling a first portion of an overhead condensate from the SRC as liquid reflux to the SRC and recycling a second portion of the overhead condensate into the pre-distillation column; and
(i) withdrawing a bottom stream from the pre-distillation column that consists essentially of water.

In yet another embodiment, the invention is directed to an improved process for dehydrating an aqueous feedstock containing ethanol and water that includes the steps of
(a) distilling an aqueous feedstock comprising ethanol and water in a pre-distillation column to produce a first vaporous overhead stream, a vaporous side-cut stream, and a first liquid bottoms stream;
(b) partially condensing the first vaporous overhead stream in a first condenser to yield a condensate phase and a vapor phase;
(c) recycling the condensate phase from the first condenser into the pre-distillation column as reflux;
(d) introducing the vaporous side-cut stream into a middle portion of an extractive distillation column (EDC);
(e) introducing a bottoms stream from a solvent recovery column (SRC) which contains a high-boiling ethanol selective solvent into an upper portion of the EDC to contact the vaporous side-cut stream under extractive distillation conditions to produce a second vaporous overhead stream that comprises water and ethanol and a second liquid bottom streams that comprises ethanol and the high-boiling ethanol selective solvent wherein the EDC is operated with a liquid reflux-to-distillate ratio of less than about 0.5;
(f) recycling at least a portion of the second vaporous overhead stream from the EDC in the form of condensate into the pre-distillation column;
(g) introducing at least a portion of the second liquid bottoms stream from the EDC that comprises ethanol and high-boiling ethanol selective solvent into the SRC to yield an overhead ethanol product that comprises greater than 99.5 weight percent ethanol and a bottoms stream that comprises high-boiling ethanol selective solvent;
(h) recycling at least a portion of the SRC bottoms stream comprising the high-boiling ethanol selective solvent into an upper portion of the EDC;
(i) recycling a portion of the ethanol product in the form of condensate into the SRC as reflux; and
(j) withdrawing a bottoms stream from the pre-distillation column that consists essentially of water.

DETAILED DESCRIPTION OF THE INVENTION

In conventional distillation, the liquid reflux at the top of distillation column governs the amount of liquid phase that is in equilibrium with the rising vapor phase at each of the contacting stages in the column. Depending on the feed composition, the product requirements, and the vapor liquid equilibrium curve (VLE) of the key components being separated, the reflux to distillate (R/D) ratio may range from 1 to 10 or even higher and typically ranges from 2 to 5. Therefore, the R/D ratio is the major operating variable that determines not only the product purity and recovery but the process energy requirements as well since the liquid reflux has to be vaporized in the column.

The present invention is based, in part, on the discovery that, in extractive distillation (ED), the ED solvent that is fed to the upper portion (near the top) of an extraction distillation column (EDC) can serve as the liquid phase as it descends down the column and is in equilibrium with the ascending vapor phase at each stage in the column. Hence, the liquid reflux which dictates the major energy requirement of the distillation column has essentially no functional purpose in the EDC.

Low-Energy Extractive Distillation Scheme for Dehydration of Aqueous Ethanol

Figure 1:
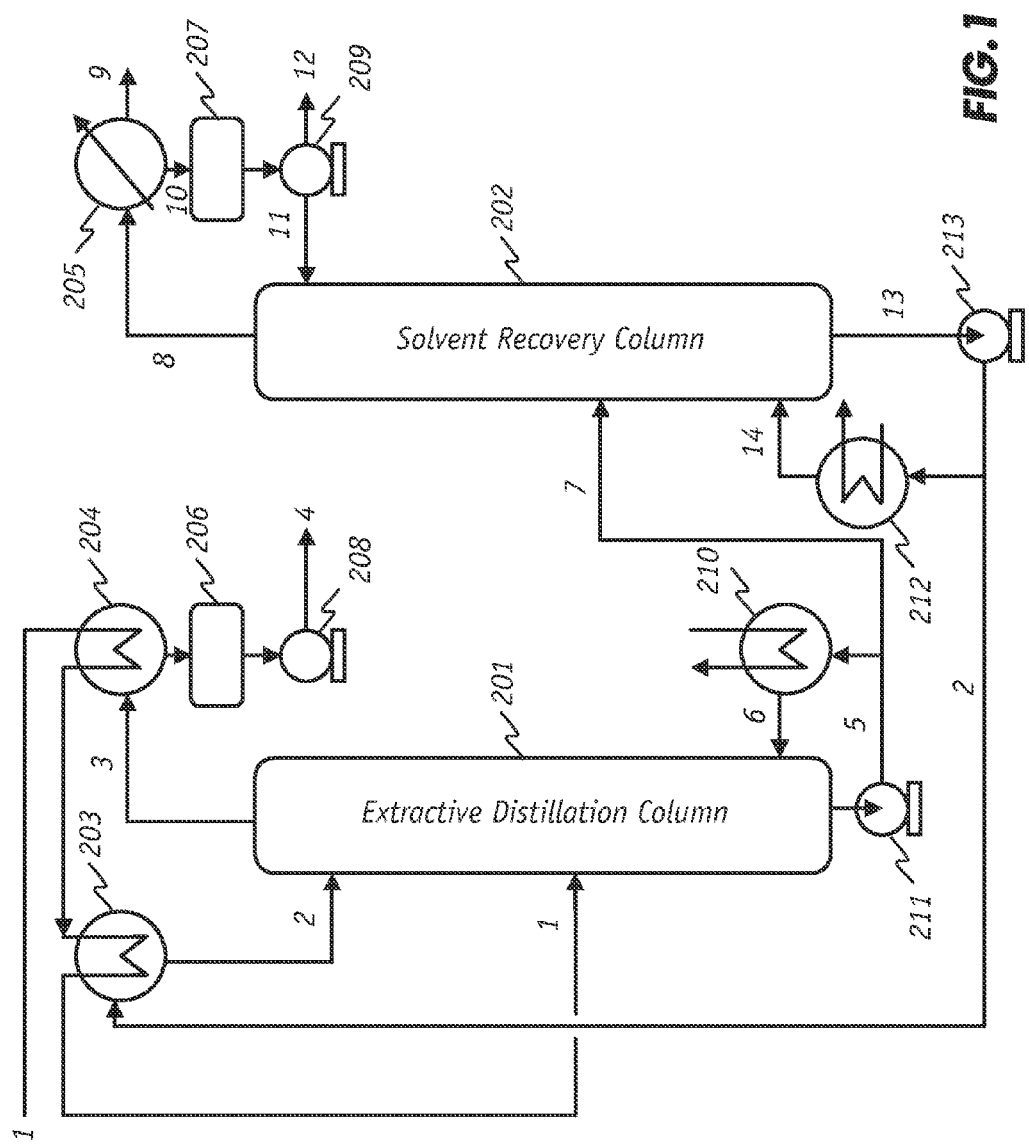
FIG. 1 illustrates a low-energy extractive distillation process for the dehydration of aqueous ethanol.

Referring to the process shown in FIG. 1, an aqueous ethanol feed is fed via line or stream 1 to the middle portion of extractive distillation column (EDC) 201. The feed contains typically 10 to 95 wt % ethanol, preferably 85 to 95 wt % ethanol, and more preferably 90 to 92 wt % ethanol. In a preferred but optional embodiment, feed stream 1 is initially heated by the EDC overhead vapor in condenser 204 before being partial or totally vaporized by the lean solvent feed to the EDC in cooler 203. Lean solvent from the bottom of solvent recovery column (SRC) 202 is fed via lines 13 and 2 into an upper portion of EDC 201 after being cooled in cooler 203. The lean solvent entry point in EDC 201 is selected at a location such that there are a few trays above the solvent tray to essentially eliminate entrained solvent that is carried over to the EDC overhead. Overhead vapor exiting EDC 201 via line 3 is condensed in condenser 204 and the condensate is transferred into accumulator 206. Preferably, no liquid reflux is recycled to the top of EDC 201 although a reflux-to-distillate (R/D) ratio ranging from 0 to less than 0.5 can be used for non-functional purposes, such as for knocking down entrained solvent from the overhead vapor stream 3. If necessary, the lean solvent temperature can be maintained 20° C. and preferably 10° C. below the EDC temperature near the solvent tray in order to generate internal reflux without expending energy.

If the high-boiling ED solvent that is used preferentially extracts water in EDC 201, ethanol product with 99.5+ wt % purity is withdrawn from accumulator 206 by pump 208 through line 4. On the other hand, if the high-boiling ED solvent that is used preferentially extracts ethanol in EDC 201, a stream consisting essentially of water is withdrawn from accumulator 206 by pump 208 through line 4. To ensure that the overhead stream 3 is not contaminated with entrained solvent when the system is operating under no reflux conditions, the preferred high-boiling ED water selective solvent that is employed for preferentially extracting water in EDC 201 preferably has a boiling point of at least 200° C. and is selected from glycerin, ethylene glycol, diethylene glycol, triethylene glycol, tetraethylene glycol, trimethylene glycol, 1,4 butanediol, and combinations thereof. On the basis of their boiling points and selectivity, the preferred solvents are glycerin, tetraethylene glycol, and ethylene glycol, and diethylene glycol.

Preferred high boiling ED ethanol selective solvent for preferentially extracting ethanol in the EDC preferably has a boiling point of at least 200° C. and is selected from of $C_6+$ phenols (including 2-phenyl-phenol, cumyl phenol, diisopropyl phenol and mixtures thereof), cyclic $C_7$ ketones (including cyclohexyl cyclohexanone), cyclic $C_8$ alcohols (including cyclohexyl cyclohexanol), methyl benzoate, dipropylene glycol dibenzoate, trimellitic anhydride, and mixtures thereof. Solvents that contain sulfur should not be used.

To keep the bottom temperature of EDC 201 at less than 200° C. and preferably in the range of 160° C. to 180° C. in order to minimize solvent decomposition, EDC 201 is operated under slightly positive pressures. Depending upon the solvent function for extracting water or ethanol, rich solvent saturated with ethanol or water, respectively, is withdrawn from the bottom of EDC 201 with pump 211 via line 5. A portion of the bottoms is passed through reboiler 210 and recycled to the bottom of EDC 201 via line 6 to maintain the vapor flow in the column. Since there is minimal or no reflux in EDC 201, the energy requirement for reboiler 210 is substantially reduced.

Rich solvent stream from EDC 201 in the form of a partially vaporized mixture is fed via lines 5 and 7 to the middle portion of solvent recovery column (SRC) 202, which is operated at reduced pressures (vacuum) to maintain the bottom temperature at below 200° C. and preferably in the range of 160° C. to 180° C. in order to minimize solvent decomposition. A vapor stream containing essentially pure water or ethanol, depending upon the solvent function, exits the top of SRC 202 via line 8 and is condensed in condenser 205. Pressure in condenser 205 as well as the top of SRC 202 typically ranges from 50 to 500 mmHg (absolute) and preferably from 150 to 300 mmHg (absolute), depending upon the boiling point of the solvent. The SRC 202 overhead is connected to a vacuum source (not shown), which can be a vacuum pump or steam ejector, through line 9. The condensate from condenser 205 is transferred via line 10 to accumulator 207, where a portion of the condensate is recycled through pump 209 to the top of SRC 202 via line 11 as a liquid reflux to provide liquid flow for the upper portion of SRC 202. The remaining portion of the condensate is withdrawn from accumulator 207 with pump 209 via line 12 in the form of water or the anhydrous ethanol product, again, depending on the solvent function.

In the meantime, lean solvent is withdrawn from the bottom of SRC 202 with pump 213 via line 13. A portion of this lean solvent is heated in reboiler 212 and recycled to the bottom of SRC 202 via line 14 to maintain the bottoms temperature in the desired temperature range. In the case where the anhydrous ethanol product is produced from the overhead of EDC 201, maintaining the bottoms temperature within these ranges keeps the water content in the lean solvent below 1 wt % and preferably in the range of 0.2 to 0.5 wt %. Higher water content in the lean solvent would lower the ethanol product purity since the lean solvent is fed to near the top of EDC 201.

Figure 2:
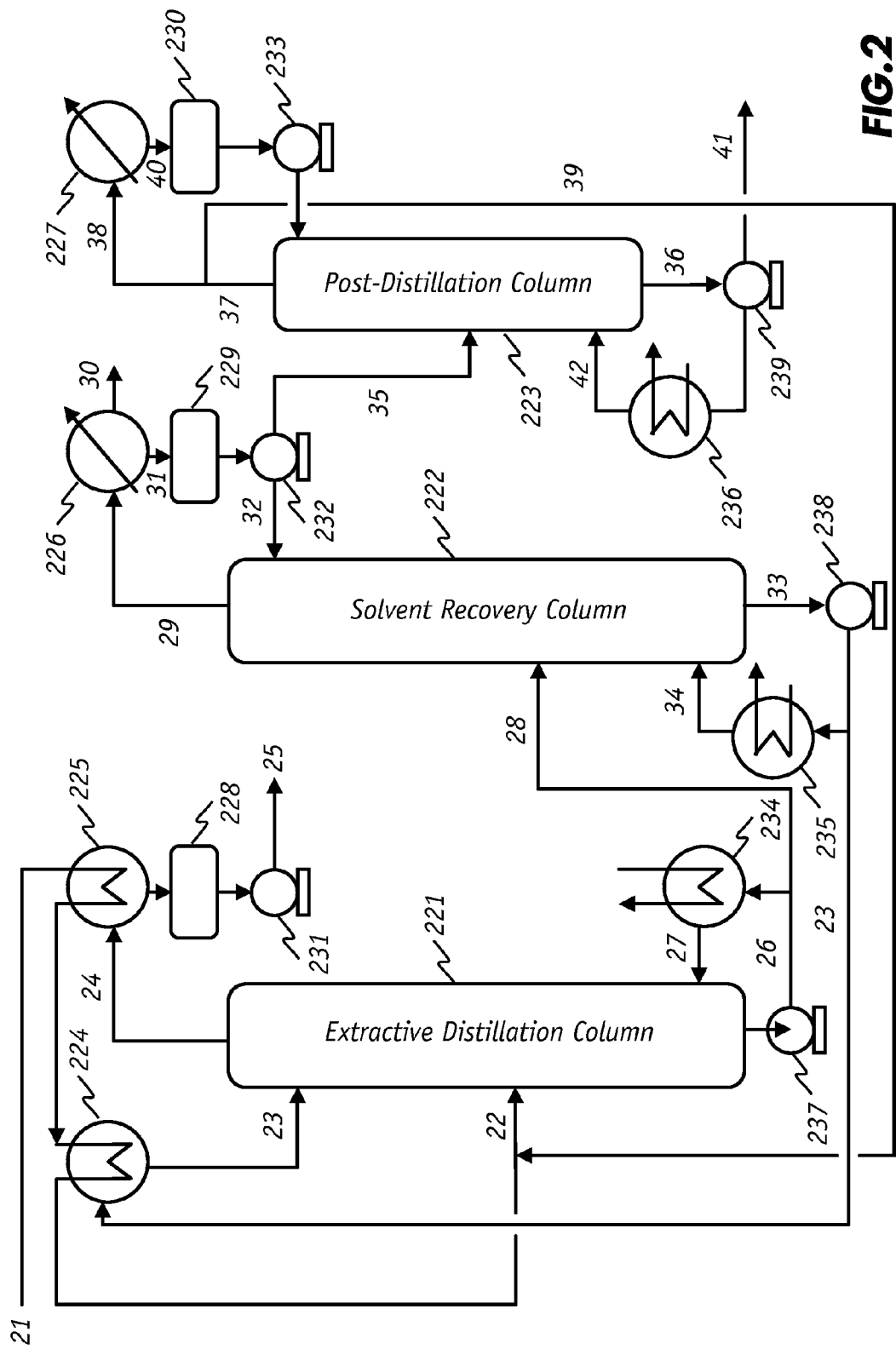
FIGS. 2 and 3 illustrate extractive distillation processes having a post-distillation column for dehydrating aqueous ethanol using high-boiling water selective solvents and using high-boiling ethanol selective solvents, respectively.

Extractive Distillation Scheme with a Post-Distillation Column for Dehydration of Aqueous Ethanol Using Water Selective Solvents FIG. 2 shows an integrated process for dehydrating aqueous ethanol that employs a system which includes an EDC 221, SRC 222, and a post-distillation column (Post-DC) 223 wherein the ED solvent used preferentially extracts water in the EDC. Again, aqueous ethanol feed containing 10 to 95 wt % ethanol, preferably 85 to 95 wt % ethanol, and more preferably 90 to 92 wt % ethanol is fed into EDC 221 via lines or streams 21 and 22. In a preferred but optional embodiment, feed stream 21 is initially heated by the EDC overhead vapor which is circulated through condenser 225 before being partial or totally vaporized by the lean solvent feed that is circulated through cooler 224.

Lean solvent from the bottom of SRC 222 is fed via lines 33 and 23 into an upper portion of EDC 221 after being cooled in cooler 224. The lean solvent entry point in EDC 221 is selected at a location such that there are a few trays above the solvent tray to essentially eliminate entrained solvent that is carried over to the EDC overhead. Overhead vapor exiting EDC 221 via line 24 is condensed in condenser 225 and the condensate is transferred into accumulator 228. Preferably, no liquid reflux is recycled to the top of EDC 221 although a reflux-to-distillate ratio ranging from 0 to less than 0.5 can be used for non-functional purposes, such as for knocking down entrained solvent from the overhead vapor stream 24. If necessary, the lean solvent temperature can be maintained 20° C. and preferably 10° C. below the EDC temperature near the solvent tray in order to generate internal reflux without expending energy. Ethanol product with 99.5+ wt % purity is withdrawn from accumulator 228 by pump 231 through line 25.

To keep the bottom temperature of EDC 221 at less than 200° C. and preferably at less than 180° C. in order to minimize solvent decomposition, EDC 221 is operated under slightly positive pressures. Rich solvent saturated with water is withdrawn from the bottom of EDC 221 with pump 237 via line 26. A portion of the bottoms is passed through reboiler 234 and recycled to the bottom of EDC 221 via line 27 to maintain the vapor flow in the column.

In this process, EDC 221 is configured to produce an ethanol product with 99.5+ wt % purity in the overhead and to allow a certain amount of ethanol in the bottoms. EDC 221 operates without liquid reflux (or minimal reflux) and requires fewer separation stages and a lower solvent-to-feed (S/F) ratio. The EDC bottoms contains preferably no more than 20 wt % and more preferably no more than 5 wt % of the ethanol that is in the feed to EDC 221. The preferred operating conditions of EDC 221 and SRC 222 are similar to those disclosed for EDC 201 and SRC 202, respectively, for the process shown in FIG. 1.

Rich solvent stream from EDC 221 in the form of a partially vaporized mixture is fed via lines 26 and 28 to the middle portion of SRC 222, which is operated at reduced pressures (vacuum) to maintain the bottom temperature at below 200° C. and preferably in the range of 160° C. to 180° C. in order to minimize solvent decomposition. Overhead aqueous vapor stream from SRC 222, which contains water and a certain amount of ethanol, is transferred via line 29 to condenser 226 under reduced pressure (vacuum), where the condensate is transferred to accumulator 229 via line 31. SRC 222 overhead is connected to a vacuum source (not shown) such as a vacuum pump or steam injector through line 30. At least a portion of the condensate is recycled to SRC 222 as liquid reflux by pump 232 via line 32. The remaining portion of the condensate is fed to Post-DC 223 via line 35 to recover ethanol. Based on VLE curves for water and ethanol mixtures, Post-DC 223 can be operated favorably to produce pure water in the bottoms and a vapor mixture of water and ethanol in the overhead stream, which exits via line 37; at least a portion of the overhead vapor in line 38 is condensed in condenser 227 and sent to accumulator 230 via line 40 and then recycled to Post-DC 223 as liquid reflux through pump 233. In order to recycle the remaining portion of overhead vapor stream from Post-DC 223 to EDC 221 via lines 39 and 22 to recover ethanol, Post-DC 223 is operated at higher pressures than that of EDC 221. The bottoms stream of Post-DC 223 containing pure water is withdrawn by pump 239 via line 36. A portion of this bottoms stream is heated by reboiler 236 and recycled to the bottom of Post-DC 223 for generating the vapor flow whereas the rest of stream 36 is withdrawn via line 41 for disposal.

In the meantime, lean solvent is withdrawn from the bottom of SRC 222 with pump 238 via line 33. A portion of this lean solvent is heated in reboiler 235 and recycled to the bottom of SRC 222 via line 34 to maintain the bottoms temperature in the desired temperature range.

Figure 3:
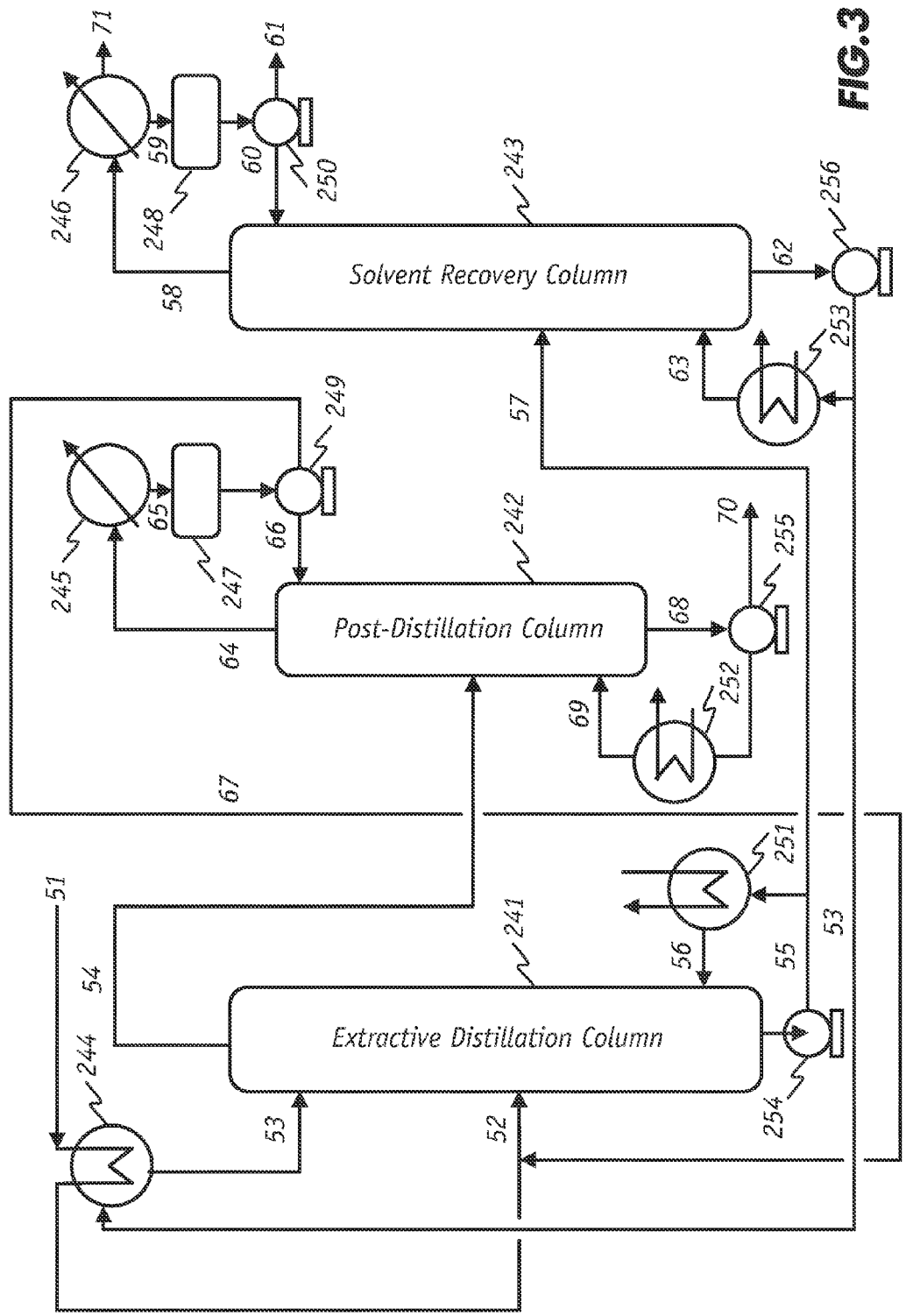

Extractive Distillation Scheme with a Post-Distillation Column for Dehydration of Aqueous Ethanol Using Ethanol Selective Solvents FIG. 3 shows an integrated process for dehydrating aqueous ethanol in a system that includes an EDC 241, SRC 243, and a Post-DC 242 wherein the ED solvent used preferentially extracts ethanol in EDC 241. An aqueous ethanol feed is fed via lines or streams 51 and 52 to the middle portion of extractive distillation column 241. The feed contains typically 10 to 95 wt % ethanol, preferably 85 to 95 wt % ethanol, and more preferably 90 to 92 wt % ethanol. In a preferred but optional embodiment, feed stream 51 is partial or totally vaporized by the lean solvent feed to EDC 241 in cooler 244. Lean solvent from the bottom of SRC 243 is fed via lines 62 and 53 into an upper portion of EDC 241 after being cooled in cooler 244. The lean solvent entry point in EDC 241 is selected at a location such that there are a few trays above the solvent tray to essentially eliminate entrained solvent that is carried over to the EDC overhead.

In this scheme, EDC 241 is configured to produce a rich solvent containing only solvent and ethanol in the bottom of EDC 241 and to allow a certain amount of ethanol in the overhead aqueous stream so that EDC 241 can be operated without liquid reflux (or minimal flux) and under much less demanding conditions of lower S/F and fewer separation stages. The overhead stream from EDC 241 contains preferably no more than 20 wt % and more preferably no more than 5 wt % of the ethanol in the feed to EDC 241. Rich solvent saturated with ethanol is withdrawn from the bottom of EDC 241 with pump 254 via line 55. A portion of the bottoms is passed through reboiler 251 and recycled to the bottom of EDC 241 via line 56 to maintain the vapor flow in the column. The preferred operating conditions of EDC 241 are similar to those described for EDC 201 in the process shown in FIG. 1.

The overhead aqueous vapor stream from EDC 241 containing water and a certain amount of ethanol is fed via line 54 to Post-DC 242. Again, Post-DC 242 can be operated favorably to produce pure water in the bottoms and a vapor mixture of water and ethanol in the overhead stream, which exits via line 64 and is condensed in condenser 245 and transferred to accumulator 247 via line 65. At least a portion of the condensate is recycled to Post-DC 242 as liquid reflux via line 66 by pump 249. The remaining portion of the condensate is recycled to EDC 241 via lines 67 and 52 to recover the ethanol. The bottoms stream of Post-DC 242 containing pure water is withdrawn by pump 255 via line 68 and a portion is disposed of through line 70 and the remaining portion is heated in reboiler 252 before being recycled back into Post-DC 242 via line 69. In order to feed the overhead vapor of EDC 241 into column Post-DC 242, EDC 241 is operated at higher pressures than that of Post-DC 242. EDC 241 bottom (rich solvent) stream containing only ethanol and solvent is withdrawn by pump 254 and fed into SRC 243 via lines 55 and 57. The preferred operating conditions of SRC 243 are similar to those disclosed in the description of SRC 202 in FIG. 1, to maintain the bottom temperature at below 200°C. and preferably in the range of 160° C. to 180° C. to minimize solvent decomposition.

A vapor stream containing essentially of pure ethanol exits the top of SRC 243 via line 58 and is condensed in condenser 246. The pressure in condenser 246 as well as at the top of SRC 243 ranges from 50 to 500 mmHg (absolute) and preferably from 150 to 300 mmHg (absolute), depending upon the boiling point of the solvent. SRC 243 overhead is connected to a vacuum source (not shown), which can be a vacuum pump or steam ejector, through line 71. The condensate from condenser 246 is transferred via line 59 to accumulator 248, where a portion of the condensate is recycled through pump 250 to the top of SRC 243 via line 60 as a liquid reflux to provide liquid flow for the upper portion of SRC 243. The remaining portion of the condensate is withdrawn from accumulator 248 with pump 250 via line 61 in the form of anhydrous ethanol.

In the meantime, lean solvent is withdrawn from the bottom of SRC 243 with pump 256 via line 62. A portion of this lean solvent is heated in reboiler 253 and recycled to the bottom of SRC 243 via line 63 to maintain the bottoms temperature in the desired temperature range.

Figure 4:
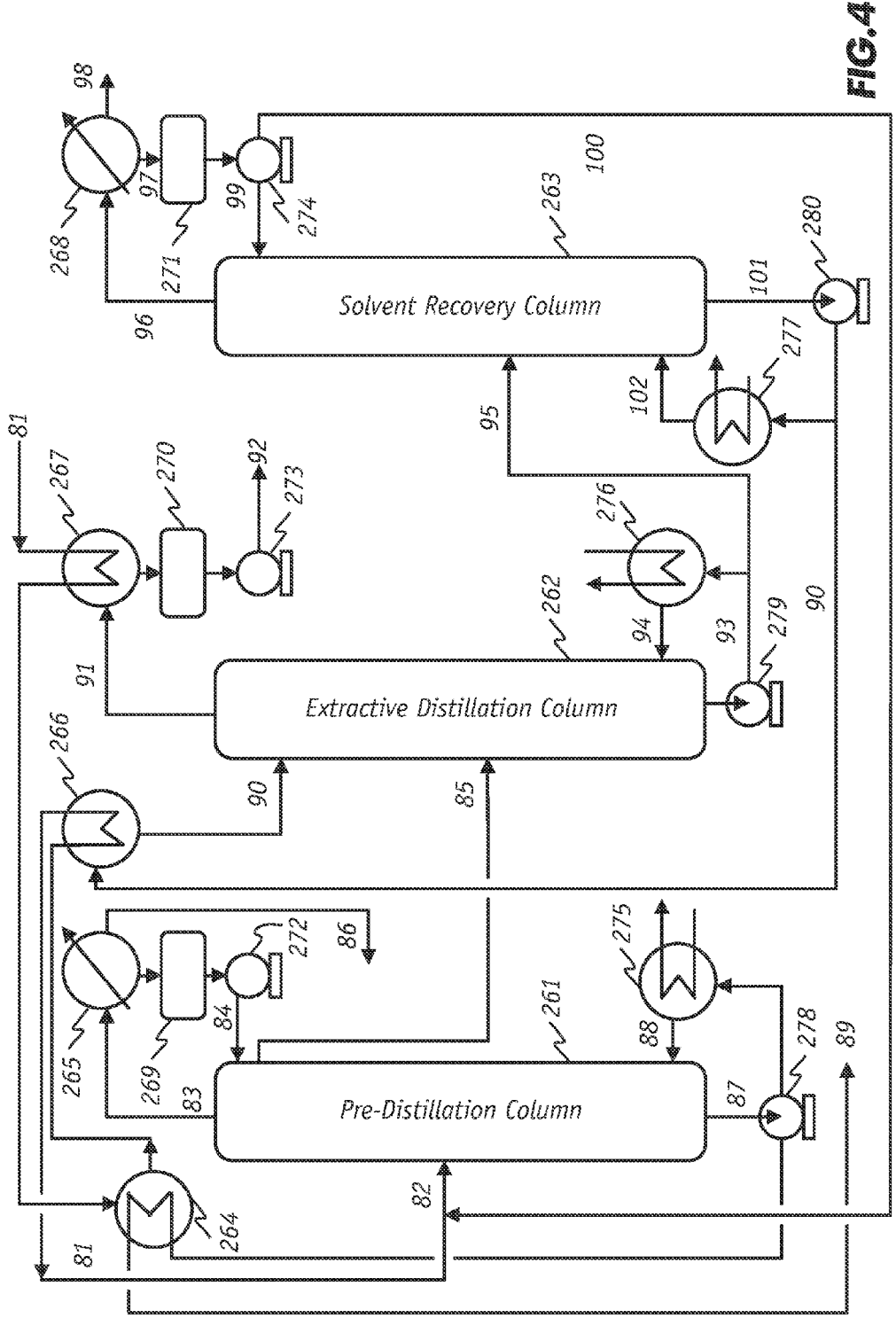
FIGS. 4 and 5 illustrate extractive distillation processes having pre-distillation column for dehydrating fermentation broth using high-boiling water selective solvents and high-boiling ethanol selective solvents, respectively.

Extractive Distillation Scheme with a Pre-Distillation Column for Dehydration of Fermentation Broth Using Water Selective Solvents FIG. 4 shows an integrated process for dehydration of fermentation broth where the ED solvent used preferentially extracts water in the EDC. The system includes a Pre-Distillation Column (Pre-DC) 261, EDC 262 and SRC 263. Fermentation broth, which typically contains 10 to 12 wt % ethanol, is fed via lines 81 and 82 into the middle portion of Pre-DC 261. In a preferred but optional embodiment, feed stream 81 is initially heated by the EDC overhead vapor that is circulated into condenser 267 and subsequently heated by the energy from the bottoms water stream from Pre-DC 261 in heat exchanger 264 before being partial or totally vaporized by the lean solvent feed to the EDC through heat exchanger 266. A vaporous side-cut stream containing 80 to 95 wt % ethanol, preferably 85 to 92 wt % ethanol, and more preferably 90 to 92 wt % ethanol is withdrawn from Pre-DC 261 from a location in Pre-DC 261 that is preferably 1 or 2 trays below the top and just below the liquid reflux entry point and the vapor fed into EDC 262 as the vaporous ethanol feed. The overhead stream in line 83 comprising vaporous ethanol, water and essentially all the light minor components including formaldehyde, methanol, and light esters from the top of Pre-DC 261 passes through partial condenser 265, which is maintained at an average temperature that is from 60 to 65° C. At this temperature range, only ethanol and water are condensed and the condensate from accumulator 269 is recycled with pump 272 into Pre-DC 261 as liquid reflux via line 84. The vaporous light components, which are not suitable for human consumption, exit condenser 265 via line 86 and are subsequently condensed separately at lower temperatures.

By using glycerin or other nontoxic ED solvents, food and medicinal grade ethanol can be produced with this process. The bottoms stream from Pre-DC 261 which contains essentially water is withdrawn via line 87 by pump 278. A portion of this bottoms stream is heated in reboiler 275 and recycled into the bottom of Pre-DC 261 via line 88 whereas the remaining portion of the bottom stream is passed through heat exchanger 264 to heat the aqueous ethanol feed to Pre-DC 261 and the cooled bottoms stream is sent back to a fermentation section (not shown) via line 89. By designing the process so that the side-cut at the top of Pre-DC 261 contains no more than 92 wt % ethanol, the liquid reflux and number of trays in Pre-DC 261 are substantially reduced. It is estimated that Pre-DC 261 requires approximately 2,570 KJ/L of energy as compared to 4,000 KJ/L (a 36% increase) that is required when the side cut stream contains 95 wt % ethanol.

A vaporous side-cut from Pre-DC 261 is fed via line 85 to the middle portion of EDC 262 whereas lean solvent from the bottom of SRC 263 is fed by pump 280 via lines 101 and 90 to the upper portion of EDC 262 after being cooled in heat exchanger 266. The lean solvent entry point in EDC 262 is selected so that there are a few trays above the solvent tray to essentially eliminate the presence of entrained solvent, if any, from being carried over to the overhead of EDC 262. Preferably, no liquid reflux is recycled back to the top of EDC 262 although a reflux-to-distillate ratio ranging from 0 to less than 0.5 can be used for non-functional purposes, such as for knocking down any entrained solvent from the overhead vapor stream. If necessary, the lean solvent temperature can be maintained at 20° C. and preferably 10° C. below the column temperature near the solvent tray which is sufficient to generate internal reflux without additional energy input. Overhead vapor exiting the EDC 262 via line 91 is condensed in condenser 267 and then transferred into accumulator 270. An ethanol product that is 99.5+ wt % pure is withdrawn from accumulator 270 with pump 273 through line 92.

In order to achieve a 99+ wt % ethanol recovery with 99.5+ wt % purity EDC 262 must be designed with a large number of separation trays and the column would need to operate under a high solvent-to-feed ratio. To minimize capital expenditure and reduce energy requirements, alternatively, EDC 262 can be designed and operated under conditions to achieve less than total ethanol recovery. In particular, in a preferred embodiment, no more than 20 wt %, and preferably no more than 5 wt %, of the ethanol that is in the EDC feed reaches the EDC bottoms (rich solvent) stream.

The rich solvent, which contains preferably no more than 5 wt % of the ethanol in the EDC feed, is withdrawn from the bottom of EDC 262 and is fed via lines 93 and 95 by pump 279 as a partially vaporized mixture into the middle portion of SRC 263. A portion of the EDC bottoms is heated through reboiler 276 and recycled to the bottom of EDC 262 via line 94 to maintain the vapor flow in EDC 262. The bottoms temperature of EDC 262 preferably is in the range from 160° C. to 200° C. Lean solvent is withdrawn from the bottoms of SRC 263 with pump 280 via line 101. A portion of this lean solvent is heated in reboiler 277 and recycled to the bottom of SRC 263 via line 102 to maintain the bottoms temperature in the range of 160° C. to 200° C. and preferably in the range of 160 to 180° C. SRC 263 typically has an operating pressure in the range of 50 to 500 mm Hg (absolute) and preferably in the range of 150 to 300 mm Hg (absolute). Overhead aqueous vapor stream from SRC 263 is transferred via line 96 to condenser 268 under reduced pressure (vacuum), where the condensate is transferred to accumulator 271 via line 97. SRC 263 overhead is connected to a vacuum source (not shown) such as a vacuum pump or steam injector through line 98. At least a portion of the condensate is recycled to SRC 263 as liquid reflux by pump 274 via line 99. The remaining portion of the condensate is recycled to Pre-DC 261 via lines 100 and 82 to recover the ethanol.

Figure 5:
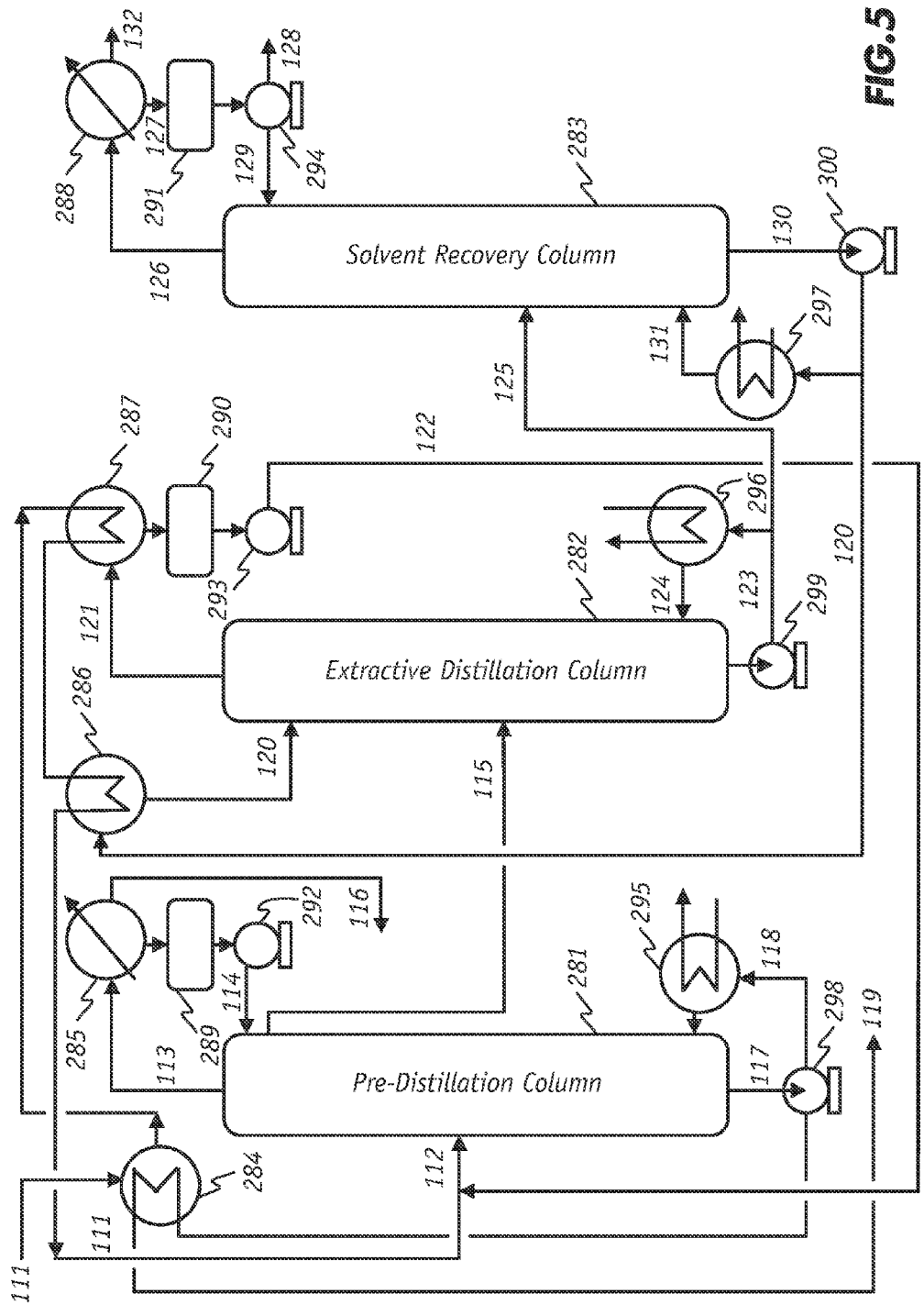

Extractive Distillation Scheme with a Pre-Distillation Column for Dehydration of Fermentation Broth Using Ethanol Selective Solvents FIG. 5 shows an integrated process for dehydration of the fermentation broth where the ED solvent used preferentially extracts ethanol in the EDC. The system includes Pre-DC 281, EDC 282, and SRC 283. Fermentation broth containing 10 to 12 wt % ethanol is fed via lines 111 and 112 into the middle portion of Pre-DC 281. In a preferred but optional embodiment, feed stream 111 is initially heated by the bottom water stream from Pre-DC 281 in heat exchanger 284 and feed stream 111 is then heated by the EDC overhead vapor which is sent through condenser 287 before being partial or totally vaporized by the EDC lean solvent feed which is sent through heat exchanger 286. Operations of the Pre-DC 281 for concentrating the fermentation broth are the same as those described for Pre-DC 261 in FIG. 4.

A vaporous side-cut stream containing 80 to 95 wt % ethanol, preferably 85 to 92 wt % ethanol, and more preferably 90 to 92 wt % ethanol is withdrawn from Pre-DC 281 from a location in Pre-DC 281 that is preferably 1 or 2 trays below the top and just below the liquid reflux entry point and the vapor fed into EDC 282 as the vaporous ethanol feed. The overhead stream in line 113 comprising vaporous ethanol, water and essentially all the light minor components including formaldehyde, methanol, and light esters from the top of Pre-DC 281 passes through partial condenser 285, which is maintained at an average temperature from 60 to 65° C. At this temperature range, only ethanol and water are condensed and the condensate from accumulator 289 is recycled with pump 292 into Pre-DC 281 as liquid reflux via line 114. The vaporous light components, which are not suitable for human consumption, exit condenser 285 via line 116 and are subsequently condensed separately at lower temperatures.

The bottoms stream from Pre-DC 281 which contains essentially water is withdrawn via line 117 by pump 298. A portion of this bottoms stream is heated in reboiler 295 and recycled into the bottom of Pre-DC 281 via line 118 whereas the remaining portion of the bottom stream is passed through heat exchanger 284 to heat the aqueous ethanol feed to Pre-DC 281 and the cooled bottoms stream is sent back to a fermentation section (now shown) via line 119. By designing the process so that the side-cut at the top of Pre-DC 281 contains no more than 92 wt % ethanol, the liquid reflux and number of trays in Pre-DC 281 are substantially reduced.

A vaporous side-cut from Pre-DC 281 is fed via line 115 to the middle portion of EDC 282 whereas lean solvent from the bottom of SRC 283 is fed by pump 300 via lines 130 and 120 to the upper portion of EDC 282 after being cooled in heat exchanger 286. The lean solvent entry point in EDC 282 is selected so that there are a few trays above the solvent tray to essentially eliminate the presence of entrained solvent, if any, from being carried over to the overhead of EDC 282.

Again, no liquid reflux is recycled back to the top of EDC 282 although a reflux-to-distillate ratio of 0 to less than 0.5 can be used for non-functional purposes, such as for knocking down any entrained solvent from the overhead vapor stream. Water vapor containing less than 20 wt % and preferably less than 5 wt % of the ethanol in the EDC feed exits the top of EDC 282 via line 121 and is condensed in heat exchanger 287. The condensate is transferred to accumulator 290 and recycled by pump 293 via lines 122 and 112 to the middle portion of Pre-DC 281 to recover the ethanol. The rich solvent, which contains substantially pure ethanol and the solvent, is withdrawn from the bottom of EDC 282 and is fed via lines 123 and 125 by pump 299 as a partially vaporized mixture into the middle portion of SRC 283. A portion of the EDC bottoms is heated through reboiler 296 and recycled to the bottom of EDC 282 via line 124 to maintain the vapor flow in EDC 282.

Overhead vapor stream from SRC 283, which contains at least 99.5 wt % ethanol, is transferred via line 126 to condenser 288 under reduced pressure (vacuum), where the condensate is transferred to accumulator 291 via line 127. SRC 283 overhead is connected to a vacuum source (not shown) such as a vacuum pump or steam injector through line 132. At least a portion of the condensate is recycled to SRC 283 as liquid reflux by pump 294 via line 129. The remaining portion of the condensate is removed via line 128 in the form of anhydrous ethanol. Lean solvent is removed by pump 300 from the bottoms of SRC 283 and a portion of the lean solvent is heated in reboiler 297 and recycled to the bottom of SRC 283 via line 131 to maintain the bottoms temperature in the range of 160 to 200° C. and preferably in the range of 160 to 180° C.

Other non-limiting operating conditions for EDC 262 and SRC 263 described for FIG. 4, such as temperature, pressure and stream flow are, respectively, adjusted for the operations of EDC 282 and SRC 283 as depicted in FIG. 5.

EXAMPLES

The following examples are presented to further illustrate the preferred embodiments of this invention and are not to be considered as limiting the scope of this invention.

Example 1

This example demonstrates that anhydrous ethanol with 99.5 wt % purity and no solvent contamination can be produced from an aqueous ethanol feed in a continuous EDC operating without liquid reflux at the top of the column. Pilot plant tests were carried out in a 3-inch (7.62 cm) diameter continuous EDC which consisted of nine (9) structurally packed sections with a chimney tray at the top of the column. It was estimated that there were four theoretical trays between the lean solvent and the ethanol feed entry points.

Aqueous feed containing 90.82 wt % ethanol and 9.18 wt % water was pre-heated to 70 to 80° C. and fed into the middle portion of the EDC ($4^{th}$ section from the bottom). A lean solvent containing 99.50 wt % glycerin and 0.50 wt % water was fed to the chimney tray at the top of the column after pre-heating. The rates of ethanol feed and glycerin solvent feed were 1.94 and 7.39 Kg/h, respectively (the overall solvent-to-feed (S/F) weight ratio was 3.8). Allowing 0.5 wt % water in the lean glycerin feed can significantly reduce the severity of the SRC operation. The EDC kettle temperature was maintained at 149° C. to generate a vapor stream in the EDC. Surprisingly, the EDC column temperature profile was within the range of 80 to 90° C. even though the boiling point of glycerin is 290° C. Even without liquid reflux at the top of the EDC, anhydrous ethanol containing 99.52 wt % ethanol, 0.48 wt % water, and no measurable levels of glycerin was produced from the EDC overhead, at a rate of 1.72 Kg/h. Rich solvent containing 96.41 wt % glycerin, 1.12 wt % ethanol, and 2.37 wt % water was withdrawn from the EDC bottom at a rate of 7.79 Kg/h. Based on experimental data, ethanol recovery was determined to be 96.2 wt %. Higher ethanol recovery can be readily achieved by using an EDC with a larger number of separation stages.

These pilot plant results demonstrate that, even when using an EDC with relatively few separation stages and operating with no liquid reflux at the top the column, a glycerin/water solvent can break the azeotrope of ethanol and water and produce anhydrous ethanol with very high purity (99.5 wt %) and no solvent contamination.

Example 2

This example demonstrates that significant energy can be saved by eliminating liquid reflux at the top of an EDC without sacrificing anhydrous ethanol purity or product recovery.

Approximately 100 kg/h of aqueous ethanol at 25° C. was fed to tray 12 (counting from the top) and 350 kg/h of glycerin solvent at 45° C. was introduced to tray 3 of an EDC consisting of 13 theoretical trays (excluding the kettle). The aqueous ethanol feed contained 90 wt % ethanol and 10 wt % water and the glycerin solvent feed contained 99.7 wt % glycerin and 0.3 wt % water. The EDC was operated with no liquid reflux and alternatively with a liquid reflux ratio (R/D) of 1.0 to compare the energy requirements of the EDC. In both cases, the column temperature increased from 78° C. at the top (tray 1) to 128° C. at the bottom (tray 13), while the column pressure increased from 1.00 to 1.25 atmospheres through the top to the bottom. The EDC kettle operated at 175° C. and 1.27 atmospheres.

Under R/D of 1.0 the energy requirement of the EDC was determined to be 2,865 KJ/L of produced anhydrous ethanol from the overhead of the EDC. Purity and recovery of the anhydrous ethanol were 99.7 wt % and 99.99 wt %, respectively. No detectable glycerin was found in the ethanol product. Under similar operating conditions for the EDC, it was found that anhydrous ethanol with 99.7 wt % purity and 99.9 wt % recovery could be produced from the overhead, without employing any liquid reflux near the top of EDC. Again, no detectable glycerin was found in the ethanol product. However, the energy requirement without the liquid reflux was significantly lower at 2,234 KJ/L (a 22% reduction).

Example 3

This ED process simulation result demonstrates that significant energy can be saved by employing partial ethanol recovery in an EDC and recovering the lost ethanol in a front-end pre-distillation (beer) column. The process simulator was upgraded and validated by the experimental data from an ED commercial demonstration plant.

Specifically, a small fraction of ethanol in ethanol feed stream to the EDC is allowed to be lost to the bottom (rich solvent) stream of the EDC. As shown in FIG. 4, the lost ethanol is then recycled and recovered in a front-end pre-distillation column where the VLE curve of ethanol/water is extremely favorable for distillation. This novel process configuration not only reduces the overall process energy requirements, but also allows the EDC to be operated under relatively mild conditions.

In accordance with the process shown to FIG. 4, 12,600 kg/h of fermentation broth containing 12 wt % ethanol and 88 wt % water is introduced into the process via line 81 and combined with a small recycled stream from SRC 263 (via line 100) before entering the middle portion of Pre-DC (PDC) 261 via line 82. The side-cut (just below the PDC reflux tray) containing approximately 90 wt % ethanol is fed to the middle portion of EDC 262 via line 85, while the lean solvent containing 99.7 wt % ethylene glycol (EG) and 0.3 wt % water is fed to near the top of EDC 262 via line 90. Solvent-to-feed weight ratio (S/F) in EDC 262 is maintained at 3.0. The EDC is operated under conditions with no ethanol loss (essentially 100% recovery) and with 2.5 wt % ethanol loss, to determine the difference in overall process energy requirements for the system which includes the PDC, EDC, and SRC process steps. The process parameters are summarized in Table 1.

TABLE 1

| 1. | Feed Flow Rate and Composition | |
|---|---|---|
| | Ethanol feed rate to PDC: | 12,600 kg/h |
| | Composition of ethanol feed to PDC: | 12 wt % ethanol and 88 wt % water |
| | Composition of ethanol feed to EDC: | 90 wt % ethanol and 10 wt % water |
| | Composition of solvent feed to EDC: | 99.7 wt % EG and 0.3 wt % water |
| | Solvent-to-feed weight ratio in EDC (S/F): | 3.0 |
| 2. | Product Flow Rate and Composition | |
| | Ethanol product rate from EDC overhead: | 1,512.45 kg/h |
| | Composition of ethanol product from EDC overhead: | 99.6 wt % ethanol and 0.4 wt % water |
| | Water rate from the process: | 11,088 kg/h |
| | Composition of water from the process: | 99.95 wt % water and 0.05 wt % ethanol |
| 3. | Number of Theoretical Stages of the Column | |
| | Pre-Distillation Column (PDC): | 50 |
| | Extractive Distillation Column (EDC): | 15 |
| | Solvent Recovery Column (SRC): | 9 |
| 4. | Column Operating Conditions | |

| | 0% Ethanol Loss in EDC | | | 2.5% Ethanol Loss in EDC | | |
|---|---|---|---|---|---|---|
| | PDC | EDC | SRC | PDC | EDC | SRC |
| Liquid Reflux (R/D) | 1.81 | 1.66 | 1.81 | 1.75 | 0.58 | 1.50 |
| Kettle Temperature (° C.) | 131.6 | 185.2 | 163.5 | 131.6 | 179.6 | 163.4 |
| Overhead Presure (atm) | 2.2 | 1.2 | 0.26 | 2.2 | 1.2 | 0.26 |
| Bottom Pressure (atm) | 2.8 | 1.8 | 0.40 | 2.8 | 1.8 | 0.40 |
| Reboiler Duty (KJ/sec) | 1,348 | 905 | 190 | 1,355 | 479 | 235 |
| Total Process Energy (KJ/h) | | 8,794,800 | | | 7,448,400 | |
| Unit Product Energy (KJ/L) | | 4,565 | | | 3,867 | |

The data presented in Table 1 show that about a 15.3% reduction in energy of the integrated process consisting of PDC, EDC, and SRC can be achieved by lowering the ethanol recovery in the EDC to 97.5 wt % and recovering the lost 2.5 wt % ethanol in the front-end pre-distillation (beer) column. The unit product energy for producing anhydrous ethanol is reduced from 4,565 to 3,867 KJ/L. The reduction of ethanol recovery in the EDC also leads to a reduction in the liquid reflux in the Pre-DC, EDC, and SRC from 1.81 to 1.75, 1.66 to 0.58, and 1.81 to 1.50, respectively.

Example 4

The following comparison shows that the inventive process is significantly more energy efficient than any of the current commercial methods of anhydrous ethanol production.

Some early studies concluded that azeotropic distillation to be more energy efficient than extraction distillation. For example, Black et al, "Extractive and Azeotropic Distillation," Am. Chem. Soc. Advances in Chemistry Series No. 115, 1-16 (1972), produced anhydrous ethanol from an aqueous ethanol feed by extractive distillation using ethylene glycol as the solvent and by azeotropic distillation using n-pentane as the entrainer. In this comparison, the RID ratio of the extractive distillation column was set at 1.8, which is equivalent to a reflux-to-feed ratio of 1.55 as described in the article. Black et al concluded that azeotropic distillation was more energy efficient.

This conclusion is flawed because the investigators designed the extractive distillation column with an exceedingly high R/D ratio of 1.8 and charged the column with an aqueous ethanol feed that contained an unnecessarily high ethanol concentration of 85.64 mole % or 93.84 wt %. Although azeotropic distillation requires a feed with a composition that is near that of an azeotropic mixture of ethanol and water, i.e., 95.6 wt % ethanol, extractive distillation has virtually no restrictions on the feed composition. This important difference means that much more energy is expended with azeotropic distillation in the pre-distillation process. As evidenced by the data in FIG. 1 of U.S. Pat. No. 4,559,109 to Lee et al, in concentrating fermentation broth with 10-12 wt % ethanol to the azeotrope level of 95.6 wt %, the first stage of raising the concentration from 10-12 wt % to 92 wt % consumes only 47% of the total distillation energy whereas the final stage of raising the concentration from 92 to 95.6 wt % consumes 53% of the total energy.

It is apparent that Black et al. did not recognized that by concentrating the feed stock to only 90 wt %, instead of 93.8 wt % and by operating the extractive distillation column with minimal or no liquid reflux, extractive distillation is clearly more economical than azeotropric distillation. An estimate of the energy requirements for producing anhydrous ethanol from fermentation broth confirms the significant advantages of using extraction distillation where the feed stock has a lower ethanol concentration over competing processes that employ a similar feed stock with a higher ethanol concentration. The results are summarized in Table 2.

TABLE 2

Comparison of Energy Consumption of Leading Ethanol Purification Technologies (Unit: KJ/Liter of Product)

| Technology | Distillation from 10 to 95 vol % | Dehydration | Total Energy |
| --- | --- | --- | --- |
| Azeotropic Distillation | 3,689 | 2,573 | 6,262* |
| PSA (Molecular Sieves) | 3,689 | 1,000 | 4,689** |
| Inventive ED Process | 2,532 (to 90 vol %) | 1,335 | 3,867*** |

In all cases, vapor from overhead of the pre-ditillation column is fed to the dehydration unit directly without condensing to save the vaporization energy.
*Values are taken from the SRI report.
**Values are estimated from published data of the most advanced pressure swing adsorption (PSA) process.
***Energy requirement for the ED process with R/D of 0.58 and partial ethanol recovery (97.5 wt %) in the EDC, which can be further reduced when R/D is decreased to zero.

In this comparison, energy consumptions were estimated for azeotropic distillation and adsorptive techniques, i.e., molecular sieves. In these conventional processes, a pre-distillation step raises the ethanol concentration from 10 to 95 vol % and, thereafter, a dehydration step completes the process to yield the anhydrous ethanol. For the inventive extractive distillation process, pre-distillation requires less energy since it raises the ethanol concentration to only 90 vol %. In this example, the calculation is based on a design whereby the R/D ratio in the extractive distillation column is 0.58. The energy requirement can be substantially lowered by employing less or no reflux. Even with R/D ratio of 0.58, the ED process of this invention requires the lowest energy among all major commercial technologies, just 3,867 KJ/L.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. An improved extractive distillation (ED) process for dehydrating an aqueous feedstock containing ethanol and water that comprises the steps of:
  (a) introducing an aqueous feedstock comprising ethanol and water into a middle portion of an extractive distillation column (EDC);
  (b) introducing a high-boiling water selective, salt-free solvent into an upper portion of the EDC to contact the aqueous feedstock under extractive distillation conditions to produce a liquid bottoms stream that comprises water and high-boiling water selective solvent and to produce a vaporous overhead stream that comprises greater than 99.5 weight percent ethanol, wherein the EDC is operated with no liquid reflux at the top of the EDC;
  (c) withdrawing at least a portion of the vaporous overhead from the EDC as a purified ethanol product;
  (d) feeding at least a portion of the liquid bottoms stream of the EDC into a solvent recovery column (SRC) to remove water therefrom and to yield a lean high-boiling water selective solvent stream; and
  (e) recycling at least a portion of the lean high-boiling water selective solvent stream into the upper portion of the EDC wherein step (a) comprises forming a liquid bottoms stream comprising water, ethanol, and high-boiling water selective solvent and in step (d) the SRC produces an overhead stream comprising water and ethanol that is condensed to form a condensate that is fed into a distillation column to yield a liquid bottoms stream consisting essentially of water and an overhead stream comprising ethanol and water which is recycled to the EDC.

2. The process of claim 1 wherein the aqueous feedstock, prior to being introduced into the EDC, is initially preheated by the vaporous overhead stream and subsequently preheated by the lean high-boiling water selective solvent stream that is recycled to the upper portion of the EDC.

3. The process of claim 1 wherein the aqueous feedstock comprises 85 to 95 wt % ethanol.

4. The process of claim 3 wherein the aqueous feedstock comprises 90 to 92 wt % ethanol.

5. The process of claim 1 wherein the high-boiling water selective, salt-free solvent is selected from the group consisting of glycerin, tetraethylene glycol, ethylene glycol, diethylene glycol, and mixtures thereof.

6. The process of claim 5 wherein the high-boiling water selective, salt-free solvent is glycerin and the purified ethanol product is food-grade ethanol.

7. The process of claim 1 wherein step (b) comprises introducing a high-boiling water selective, salt-free solvent through an entry point at the upper portion of the EDC wherein the temperature of the high-boiling water selective solvent is about 10° C. to 20° C. lower than that of the EDC at the entry point in order to generate internal reflux.

8. The process of claim 1 wherein the lean high-boiling water selective solvent which is removed from a bottom of the SRC has less than about 0.5 wt % water.

9. The process of claim 1 wherein the EDC has a bottoms temperature in a range of 160° C. to 200° C.

10. The process of claim 1 wherein the SRC has a bottoms temperature in a range of 160° C. to 200° C.

11. The process of claim 1 wherein the SRC has an operating pressure in a range of 50 to 500 mmHg (absolute).

12. The process of claim 11 wherein the SRC has an operating pressure in a range of 150 to 300 mmHg (absolute).

13. The process of claim 1 wherein the amount of ethanol that is in the liquid bottoms stream of the EDC is less than about 0.5 wt % of the amount of ethanol that is in the aqueous feedstock.

14. The process of claim 1 wherein the amount of ethanol that is in the liquid bottoms stream of the EDC is about 20 wt % of the amount of ethanol that is in the aqueous feedstock.

15. The process of claim 1 wherein the amount of ethanol that is in liquid bottoms stream of the EDC is no more than about 5 wt % of the amount of ethanol that is in the aqueous feedstock.

16. An improved extractive distillation (ED) process for dehydrating an aqueous feedstock containing ethanol and water that comprises the steps of:
   (a) introducing an aqueous feedstock comprising ethanol and water into a middle portion of an extractive distillation column (EDC);
   (b) introducing a high-boiling ethanol selective, salt-free solvent into an upper portion of the EDC to contact the aqueous feedstock under extractive distillation conditions to produce a liquid bottoms stream consisting essentially of ethanol and high-boiling ethanol selective solvent and a vaporous overhead stream consisting essentially of water, Wherein the EDC is operated with no liquid reflux at the top of the column;
   (c) feeding at least a portion of the liquid bottoms stream of the EDC into a solvent recovery column (SRC) to remove ethanol therefrom and to yield a bottoms stream that comprises lean high-boiling ethanol selective solvent and an overhead stream whereby at least a portion of the overhead is withdrawn as a purified ethanol product with higher than 99.5 wt % purity; and
   (d) recycling at least a portion of the lean high-boiling ethanol selective solvent from the bottoms stream of the SRC into the upper portion of the EDC wherein step (b) comprises introducing a high-boiling ethanol selective, salt-free solvent through an entry point at the upper portion of the EDC wherein the temperature of the high-boiling ethanol selective solvent is about 10° C. to 20° C. lower than that of the EDC at the entry point in order to generate internal reflux.

17. The process of claim 16 wherein the aqueous feedstock, prior to being introduced into the EDC, is initially preheated by the vaporous overhead vapor stream and subsequently preheated by lean high-boiling ethanol selective solvent that is recycled to the upper portion of the EDC.

18. The process of claim 16 wherein the aqueous feedstock comprises 85 to 95 wt % ethanol.

19. The process of claim 18 wherein the aqueous feedstock comprises 90 to 92 wt % ethanol.

20. The process of claim 16 wherein the high-boiling ethanol selective, salt-free solvent is selected from the group consisting of 2-phenyl-phenol, cumyl phenol, diisopropyl phenol, cyclohexyl cyclohexanone, cyclohexyl cyclohexanol, methyl benzoate, dipropylene glycol dibenzoate, trimellitic anhydride, and mixtures thereof.

21. The process of claim 16 wherein the amount of ethanol that is in the EDC overhead stream is less than about 0.5 wt % of the amount of ethanol that is in the aqueous feedstock.

22. The process of claim 16 wherein step (a) comprises producing a vaporous overhead stream comprising water and ethanol and the process further comprises the steps of:
   (e) feeding at least a portion of the vaporous overhead stream from the EDC into a distillation column to produce a second liquid bottoms stream consisting essentially of water and a second overhead stream comprising ethanol and water; and
   (f) recycling the second overhead stream into the EDC.

23. An improved extractive distillation (ED) process for dehydrating an aqueous feedstock containing ethanol and water that comprises the steps of:
   (a) introducing an aqueous feedstock comprising ethanol and water into a middle portion of an extractive distillation column (EDC):
   (b) introducing a high-boiling ethanol selective, salt-free solvent into an upper portion of the EDC to contact the aqueous feedstock under extractive distillation conditions to produce a liquid bottoms stream consisting essentially of ethanol and high-boiling ethanol selective solvent and a vaporous overhead stream consisting essentially of water, wherein the EDC is operated with no liquid reflux at the top of the column;
   (c) feeding at least a portion of the liquid bottoms stream of the EDC into a solvent recovery column (SRC) to remove ethanol therefrom and to yield a bottoms stream that comprises lean high-boiling ethanol selective solvent and an overhead stream whereby at least a portion of the overhead is withdrawn as a purified ethanol product with higher than 99.5 wt % purity;
   (d) recycling at least a portion of the lean high-boiling ethanol selective solvent from the bottoms stream of the SRC into the upper portion of the EDC, wherein step (a) comprises producing a vaporous overhead stream comprising water and ethanol and the process further comprises the steps of;
   (e) feeding at least a portion of the vaporous overhead stream from the EDC into a distillation column to produce a second liquid bottoms stream consisting essentially of water and a second overhead stream comprising ethanol and water; and
   (f) recycling the second overhead stream into the EDC wherein the amount of ethanol that is in the vaporous overhead stream of the EDC is about 20 wt % of the amount of ethanol that is in the aqueous feedstock.

24. An improved extractive distillation (ED) process for dehydrating an aqueous feedstock containing ethanol and water that comprises the steps of:
   (a) introducing an aqueous feedstock comprising ethanol and water into a middle portion of an extractive distillation column (EDC);
   (b) introducing a high-boiling ethanol selective, salt-free solvent into an upper portion of the EDC to contact the aqueous feedstock under extractive distillation conditions to produce a liquid bottoms stream consisting essentially of ethanol and high-boiling ethanol selective solvent and a vaporous overhead stream consisting essentially of water, wherein the EDC is operated with no liquid reflux at the top of the column;
   (c) feeding at least a portion of the liquid bottoms stream of the EDC into a solvent recovery column (SRC) to remove ethanol therefrom and to yield a bottoms stream that comprises lean high-boiling ethanol selective solvent and an overhead stream whereby at least a portion of the overhead is withdrawn as a purified ethanol product with higher than 99.5 wt % purity;

(d) recycling at least a portion of the lean high-boiling ethanol selective solvent from the bottoms stream of the SRC into the upper portion of the EDC, wherein step (a) comprises producing a vaporous overhead stream comprising water and ethanol and the process further comprises the steps of;

(e) feeding at least a portion of the vaporous overhead stream from the EDC into a distillation column to produce a second liquid bottoms stream consisting essentially of water and a second overhead stream comprising ethanol and water; and (f) recycling the second overhead stream into the EDC wherein the amount of ethanol in the vaporous overhead stream of the EDC is no more than about 5 wt % of the amount of ethanol that is in the aqueous feedstock.

* * * * *